United States Patent
Garcia et al.

(10) Patent No.: US 6,362,292 B1
(45) Date of Patent: Mar. 26, 2002

(54) POLMERIZATION CATALYSTS

(75) Inventors: Eliane Garcia, Martigues (FR); Ian Raymond Little, Surrey (GB); Stephan Rodewald, Camal Fulton, OH (US)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/471,422

(22) Filed: Dec. 23, 1999

Related U.S. Application Data

(63) Continuation of application No. PCT/GB98/01847, filed on Jun. 24, 1998.

(30) Foreign Application Priority Data

Jun. 27, 1997 (GB) .............................................. 9713741

(51) Int. Cl.⁷ .............................. C08F 4/16; C08F 4/44; B01J 31/18
(52) U.S. Cl. ...................... 526/127; 526/160; 526/161; 526/943; 502/117; 502/152; 502/155; 502/104; 556/11; 556/12; 556/53
(58) Field of Search ................................. 526/127, 131, 526/133, 134, 160, 161, 943; 502/104, 117, 118, 152, 155; 556/11, 12, 53

(56) References Cited

U.S. PATENT DOCUMENTS 5,556,928 A * 9/1996 Devore et al. .............. 526/127
5,616,664 A * 4/1997 Timmers et al. ............ 526/127
6,090,962 A * 7/2000 Rosen ......................... 556/11

FOREIGN PATENT DOCUMENTS

EP 0 468 537 1/1992
EP 0 495 375 7/1992

\* cited by examiner

Primary Examiner—David W. Wu
Assistant Examiner—R. Harlan
(74) Attorney, Agent, or Firm—Finnegan, Henderson, Farabow, Garrett & Dunner, L.L.P.

(57) ABSTRACT

Transition metal complexes suitable for use for the polymerization of olefins having Lewis Base functionality. Preferred groups are dienes having dialkylamino functionality. The complexes may suitably be supported by the use of the functionalized dienes to give transition metal complexes which in the presence of activators are particularly suitable for gas phase processes.

25 Claims, No Drawings

POLMERIZATION CATALYSTS

This application is a continuation of International Application No. PCT/GB98/01847, filed Jun. 24, 1998, the content of which is incorporated herein by reference.

BACKGROUND OF THE INVENTION

The present invention relates to catalysts suitable for the polymerisation of olefins in particular to catalysts comprising supported transition metal complexes suitable for use for the polymerisation of ethylene or the copolymerisation of ethylene with alpha-olefins.

The use of transition metal complexes as components of catalyst compositions suitable for the polymerisation of olefins is well known. For example olefin polymerisation catalysts based on metallocene complexes are known. Such catalysts typically comprise bis(cyclopentadienyl)zirconium complexes together with activators such as aluminoxanes and are disclosed in detail in EP 129368 and EP 206794. When used for polymerisation in the gas phase such complexes are typically supported for example on silica.

There have however been many attempts at fixing or tethering such metallocene complexes in order to enable them to be utilised as heterogeneous catalysts for the polymerisation of olefins in particular for use in the slurry or gas phase.

EP 586 167-A1 discloses the functionalisation of metal complexes with polymerisable groups which allow the formation of metallocene containing polymers, usually low yield polyolefins, providing a method for fixing metal complexes to supports, for example silica.

U.S. Pat. No. 5,498,581 discloses the production of solid metallocene-containing catalyst systems by incorporating an olefinic group attached to a metallocene (eg (methyl-1-butenyl)methylene-bridged (cyclopentadienyl)(fluorenyl) $ZrCl_2$) into a solid prepolymer.

U.S. Pat. Nos. 5,492,973, 5,492,974, 5,492,975, 5,492,978, and 5,492,985 disclose the formation of polymer-bound ligands by the reaction of a metallated polymer (eg polystyrene) with a chlorinated cyclopentadienyl (Cp)-containing moiety, followed by reaction with a metal compound (eg $CpMCl_3$) to give a polymer-bound catalyst precursor. This method however suffers from the possible disadvantage that the ligand modification necessary to effect the polymer binding may interfere with the chemistry of the active site.

U.S. Pat. No. 5,466,766 discloses a process for preparing supported metallocene complexes by using a ligand possessing an active halogen, and reacting it with a hydroxylated support to give an immobilised complex (eg silica-O-Cp-fluorenylmethylsilane $ZrCl_2$). This method also suffers from the possible disadvantage that the ligand modification necessary to effect the polymer binding may interfere with the chemistry of the active site, and the release of polar compounds as by-products on interaction of the active halogen with the support hydroxyl functionality (eg HCl), which could act as a poison for olefin polymerisation catalyst systems.

EP 670 336-A1 discloses bridged bis-Cp complexes, eg silyl-bridged bis-indenyl zirconium chlorides, which possess alkylamino-substituents attached to the ligand, eg to the indenyl moiety. These are then reacted with a hydroxylated oxide support (eg silica) treated with halogenated silanes (eg $(RO)_3Si(4-CH_2Cl-Ph)$ and $Me_3SiCl$) in a solvent (eg toluene) to effect immobilisation via quaternisation of the amine N (eg [indenyl-$N^+(Me)_2$-$CH_2$-Ph-Si-support][$Cl^-$]).

WO 96/04319 discloses immobilisation of a borate activator to the surface of a support to form a supported borate (eg [support-O-$B(C_6F_5)_3$]$^-$[H]$^+$) with subsequent treatment with metallocene dialkyl (eg $Cp_2M(Me)_2$) to give an immobilised catalyst (eg [support-O—$B(C_6F_5)_3$]$^-$[$Cp_2M(Me)$]$^+$).

JP 1-259005 and 1-259004 disclose the preparation of complexes with ligands containing silane functionality (eg $((MeO)_3Si$—$CH_2$—$CH_2$-indenyl)$ZrCl_3$) and their use in supported catalyst formulations using hydroxylated oxide supports. One possible problem with this approach may be the release of polar compounds as by-products on interacting the silane with the support hydroxyl functionality (eg MeOH), and their role as poisons for olefin polymerisation catalyst systems.

Other complexes have been disclosed with similar functionality but which do not teach their use specifically to tether or bind the metallocene complex onto a support.

For example EP 670 325-A2 discloses bridged bis-Cp complexes, eg silyl-bridged bis-indenyl zirconium chlorides, which possess alkylamino-substituents attached to the ligand, eg to the indenyl moiety. No indication of use of the alkylamino-substituents for tethering purposes is however disclosed.

U.S. Pat. No. 5,486,585 discloses the preparation of metal complexes which possess ligands containing silyl-bridges which are amido-functionalised (eg$((Me_2N)_2Si)(2$-Me-indenyl$)_2ZrCl_2$. The complexes may be used with an activator to make a catalyst system which may be supported but few details of the preferred supporting method are disclosed.

It would be most desirable therefore to have an immobilisation method for such metallocene complexes which does not rely on chemical modification of the ligand system which remains attached to the active metal site during use as a polymerisation catalyst.

It would also be desirable to have an immobilisation method for metal complexes which does not involve the release or formation of reactive materials during the immobilisation process.

It would also be very desirable to have an immobilisation method which may be used for a wide range of metal complexes.

In recent years there have been a number of patents describing polymerisation catalyst systems based on transition metal complexes which also comprise an unsaturated moiety eg neutral conjugated or non-conjugated diene ligands which form complexes with the metal of the complex. Such catalyst systems are disclosed in WO 95/00526 and WO 96/04290 incorporated herein by reference.

SUMMARY OF THE INVENTION

We have now discovered that such complexes may be suitably supported by use of the unsaturated moiety when containing a Lewis base functionality.

Thus according to the present invention there is provided a transition metal complex suitable for use in the polymerisation of olefins comprising a transition metal complex of formula:

wherein

M is titanium, zirconium or hafnium in the +2 or +4 oxidation state,

L is a group containing a cyclic delocalised anionic π system through which the group is bound to M, Q is a moiety bound to M via a σ-bond comprising boron or a member of Group 14 of the Periodic Table and also comprising nitrogen, phosphorus, sulphur or oxygen, said moiety having up to 60 non-hydrogen atoms, x=1 or 2 y=0 or 1 such that when x=1, y=1 and when x=2, y=0, and

D is a neutral, conjugated or non-conjugated unsaturated moiety optionally substituted with one or more hydrocarbyl groups, said D having up to 40 carbon atoms and forming a π complex with M when M is in the +2 oxidation state and a σ complex with M when M is in the +4 oxidation state and having at least one Lewis Base group B.

The L group is preferably a $C_5H_4$ group bound to Q and bound in an $\eta^5$ bonding mode to M or is such an $\eta^5$ bound group substituted with from one to four substituents independently selected from hydrocarbyl, silyl, germyl, halo, cyano, and combinations thereof, said substituent having up to 20 non hydrogen atoms, and optionally, two such substituents (except cyano or halo) together cause L to have a fused ring structure.

The L group is preferably cyclopentadienyl or substituted cyclopentadienyl eg indenyl.

When the Q group is present (when y=1) it may be suitably represented as Z—Y wherein Y is —O—, —S—, —NR*—, —PR*—, and Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein:

R* each occurence is independently hydrogen, or a member selected from hydrocarbyl, silyl, halogenated alkyl, halogenated aryl, and combinations thereof, said R* having up to 10 non-hydrogen atoms, and optionally, two R* group from Z (when R* is not hydrogen), or an R* group from Z and an R* group from Y form a ring system.

Most preferred complexes are amidosilane or amidoalkanediyl complexes wherein the metal is titanium.

When there are two L groups present (ie when x=2) they may be joined together via a suitable bridging group represented by

wherein

Z is silicon, germanium or carbon, p is an integer from 1–8,

R is hydrogen or a group selected from hydrocarbyl or combinations, thereof, and L is as defined above.

Most preferred complexes of this type are those wherein M is zirconium, L is indenyl and $(R_2Z)_p$ is $CH_2CH_2$ ie Z=carbon, R=H and p=2.

DETAILED DESCRIPTION OF THE INVENTION

Typical examples of transition metal complexes suitable for use in the present invention are represented as follows. When x=1

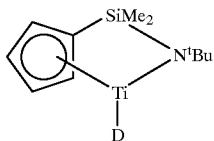

Alternatively when x=2 suitable complexes are represented by the following:

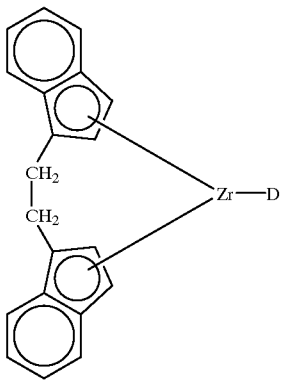

Examples of suitable unsaturated moieties include olefinic, acetylenic or imido ligands including cyclic derivatives. A particularly preferred moiety is a diene.

Examples of suitable diene groups which may contain the Lewis Base group B include s-trans-$\eta^4$1,4-diphenyl-1,3-butadiene; s-trans-$\eta^4$-3-methyl-1,3-pentadiene; s-trans-$\eta^4$-1,4-dibenzyl-1,3-butadiene; s-trans-$\eta^4$-2,4-hexadiene; s-trans-$\eta^4$-1,3-pentadiene; s-trans-$\eta^4$-1,4-ditolyl-1,3-butadiene; s-trans-$\eta^4$-1,4-bis(trimethylsilyl)-1,3-butadiene; s-cis-$\eta^4$-1,4-diphenyl-1,3-butadiene; s-cis-$\eta^4$-3-methyl-1,3-pentadiene; s-cis-$\eta^4$-2,4-hexadiene; s-cis-$\eta^4$2,4-hexadiene; s-cis-$\eta^4$1,3-pentadiene; s-cis-$\eta^4$-1,4-ditolyl-1,3-butadiene; and s-cis-$\eta^4$-1,4bis-(trimethylsilyl)-1,3-butadiene, said s-cis diene group forming a π-complex as defined herein with the metal.

Particularly suitable are the 1,4-diphenyl substituted butadienes.

The Lewis Base group B present in the unsaturated moiety may be chosen from the following groups:

—$NR_2$, —$PR_2$, $AsR_2$, —OR, —SR wherein R may be hydrogen, halogen, $C_1$–$C_{20}$ aryl, $C_7$–$C_{40}$ alkylaryl, $C_7$–$C_{40}$ arylalkyl, $C_8$–$C_{40}$ arylalkenyl and may be the same or different or may be linked to form cyclic species containing between 2–20 carbon atoms.

Suitable examples of Lewis Base groups include the following.

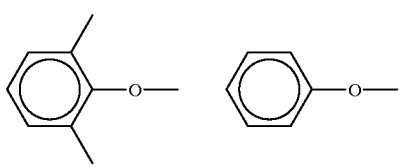

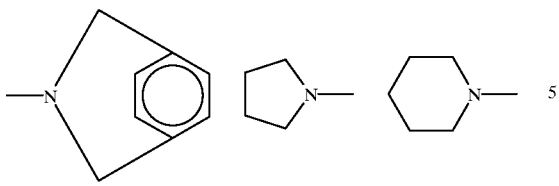

A particularly preferred diene for use as the unsaturated moiety in the present invention is 1-phenyl-4-(N,N'-dimethylaminophenyl) 1,3-butadiene represented by the formula:

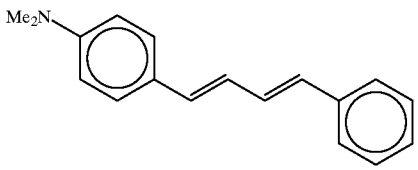

Illustrative but not limiting examples of complexes preferred are (Ethylenebis-indenyl)zirconium(Me$_2$N-dpbd) (EBIZr(Me$_2$N-dpbd))

(Tert-butylamido) ($\eta^5$-tetramethylcyclopentadienyl) dimethylsilanetitanium(Me$_2$N-dpbd)

wherein (Me$_2$N-dpbd) represents 1-phenyl-4-(4-N,N'-dimethylaminophenyl)-1,3-butadiene Another complex suitable for use in the present invention may be represented by the formula:

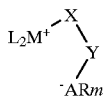

wherein

L is as described above

M is a metal atom of group IIIB, IVB, VB or VIB of the Periodic Table

X is a heteroatom or hydrocarbyl group having 1–40 carbon atoms

Y is a hydrocarbyl group having 1–40 carbon atoms, and wherein X and/or Y contain at least one Lewis Base Group B as previously defined.

A is a metal atom of Group IB, IIB, IIIA, IIIB, IVA, VA, VB, VIB, VIIB or VIIIB of the Periodic Table.

R are identical or different and are each a perhalogenated C$_1$–C$_{40}$ hydrocarbon radical, and m=1–5.

The complexes according to the present invention may suitably be supported.

Thus there is provided a supported catalyst system suitable for use in the polymerisation of olefins comprising
(A) transition metal complex of formula:

wherein

M is titanium, zirconium or hafnium in the +2 or +4 oxidation state,

L is a group containing a cyclic delocalised anionic π system through which the group is bound to M, Q is a moiety bound to M and L via a σ-bond comprising boron or a member of Group 14 of the Periodic Table and also comprising nitrogen, phosphorus, sulphur or oxygen, said moiety having up to 60 non-hydrogen atoms, x=1 or 2 y=0 or 1 such that when x=1, y=1 and when x=2, y=0, and

D is a neutral, conjugated or non-conjugated unsaturated moiety optionally substituted with one or more hydrocarbyl groups, said D having up to 40 carbon atoms and forming a π complex with M when M is in the +2 oxidation state and a σ complex with M when M is in the +4 oxidation state and having at least one Lewis Base group B, and (B) a support.

Typically the support may be any organic or inorganic inert solid particularly porous supports such as talc, inorganic oxides and resinous support materials such as polyolefins. Suitable inorganic oxide materials which may be used include Group 2, 13, 14 or 15 metal oxides such as silica, alumina, silica-alumina and mixtures thereof. Other inorganic oxides that may be employed either alone or in combination with the silica, alumina or silica-alumina are magnesia, titania or zirconia. Other suitable support materials may be employed such as finely divided polyolefins such as polyethylene.

The most preferred support material for use with the supported catalysts according to the process or the present invention is silica. Suitable silicas include Crosfield ES70 and Grace Davison 948 silicas.

It is preferable that the silica is dried before use and this is typically carried out by heating at elevated temperatures for example between 200 and 850 deg. C.

The support may preferably be treated to modify its surface properties. Suitable reagents are reactive metal and non-metal alkyl compounds, and reactive metal and non-metal hydrides, and reactive compounds containing alkyl and/or hydride functionality. Examples include magnesium alkyls, boron alkyls, aluminium alkyls, gallium alkyls, titanium alkyls, zirconium alkyls, hafnium alkyls, zinc alkyls and the corresponding hydrides and mixed alkyl hydride compounds. An example of a suitable mixed alkyl hydride compound is di-isobutylaluminium hydride.

When used as a component of a catalyst system for the polymerisation of olefins the supported complexes of the present invention are used in the presence of a suitable activator or activating technique.

Thus according to another aspect of the present invention there is provided a catalyst system suitable for the polymerisation of olefins comprising:

(a) a supported catalyst as defined above, and (b) an activator or activating technique.

The complexes may be rendered catalytically active by combination with any suitable activating cocatalyst or by use of an activating technique which are effective for the supported transition metal complexes of the present invention. Suitable activating cocatalysts for use herein include polymeric or oligomeric alumoxanes, especially methylalumoxane, triisobutyl aluminium modified methylalumoxane, or diisobutylalumoxane; strong Lewis acids, such as, C$_{1-30}$ hydrocarbyl substituted Group 13 compounds, especially tri(hydrocarbyl)aluminium- or tri (hydrocarbyl)boron compounds and halogenated derivatives thereof having from 1 to 10 carbons in each hydrocarbyl or halogenated hydrocarbyl group, more especially perfluorinated tri(aryl)boron compounds, and most especially tris (pentafluorophenyl)borane; nonpolymeric, inert, compatible, noncoordinating, ion forming compounds (including the use of such compounds under oxidising conditions); bulk electrolysis and combinations of the foregoing activating cocatalysts and techniques. The foregoing activating cocatalysts and activating techniques have been previously taught with respect to such metal complexes in the aforementioned WO 95/00526 incorporated herein by reference.

A particularly preferred activator is tris (pentafluorophenyl)boron.

Suitable ion forming compounds useful as cocatalysts comprise a cation which is a Bronsted acid capable of donating a proton, and an inert, compatible, noncoordinating, anion, A⁻. Preferred anions are those containing a single coordination complex comprising a charge-bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminium, gold and platinum. Suitable metalloids include, but are not limited to, boron, phosphorus, and silicon. Compounds containing anions which comprise coordination complexes containing a single metal or metalloid atom are available commercially particularly such compounds containing a single boron atom in the anion portion.

Preferred boron compounds are salts such as:

trityl tetrakis (pentafluorophenyl)borate triethylammonium tetrakis (pentafluorophenyl)borate N,N-dimethylanilinium tetrakis (pentafluorophenyl) borate N,N-diethylanilinium tetrakis (pentafluorophenyl)borate.

Most preferred activators of this type are trialkylammonium tetrakis (pentafluorophenyl) borates.

The molar ratio of complex to activator employed in the process of the present invention may be in the range 1:10000 to 100:1. A preferred range is from 1:5000 to 10:1 and is most preferred in the range 1:10 to 1:1.

In a preferred protocol the supported catalyst may be prepared by addition of a solution of the activator in a suitable solvent to a slurry of activated silica treated with a trialkylaluminium compound followed by addition of a solution of the metallocene complex in the same solvent.

Alternatively the complex may be added to the trialkylaluminium treated silica before addition of the activator.

Thus according to another aspect of the present invention there is provided a method for preparing a supported catalyst comprising the steps of (a) addition of an activator in a suitable solvent to a support, (b) addition of a transition metal complex as hereinbefore described to the solution obtained from step (a), and (c) removal of the solvent.

Suitable solvents for the preparation of the supported complexes are alkanes and aromatic solvents such as pentanes, hexanes, heptanes, octanes, Isopar™, toluene, xylenes, benzenes and mixtures thereof.

A particularly suitable solvent for the preparation of the supported catalyst is toluene.

Suitable trialkylaluminium compounds are trimethylaluminium (TMA), triethylaluminium(TEA) or triisobutylaluminium (TIBAL).

The supported catalyst of the present invention has the advantage of enabling the catalyst to be fixed to the support as well as greater preparation flexibility in particular increased preparative options. In addition the product morphology may be improved, fouling during the process may be reduced and both activity and productivity improved.

The supported catalyst system according to the present invention is suitable for use for the polymerisation of olefins in particularly for the homopolymerisation of ethylene or the copolymerisation of ethylene with other alpha-olefins in particular those having from 3 to 10 carbon atoms. Most preferred alpha-olefins are 1-butene, 1-hexene and 4-methyl-1-pentene.

Thus according to another aspect of the present invention there is provided a process for the polymerisation of ethylene or the copolymerisation of ethylene and alpha-olefins having from 3–10 carbon atoms comprising carrying out the process in the presence of a catalyst system comprising a supported transition metal complex and an activator as hereinbefore described.

The catalyst system according to the present invention is most suitable for use in the gas phase or slurry phase but are most suitable for use in the gas phase.

A particularly preferred process is that operating using a fluidised bed and in particular a process as described in EP 699213.

Using the supported catalyst system according to the present invention polymers may be prepared having densities in the range from 0.905 to 0.960 g/cc and a melt index in the range 0.1 to 20 according to ASTM D1238 condition E (2.16 kg. at 190 deg.C.).

The present invention will now be further illustrated with reference to the following Examples.

EXAMPLE 1

Preparation of 1-phenyl-4-(4-N,N'-dimethylaminophenyl)-1,3-butadiene (Me₂N-dpbd)

Triphenylbenzylphosphonium chloride (Aldrich, 4.044 g, 10.4 mmol) and para-N,N'-dimethylaminocinnamaldehyde (Aldrich, 1.682 g, 9.6 mmol) were dissolved in ethanol (Aldrich, dry denatured, 200 ml) under nitrogen. To the stirring solution was added lithium ethoxide (Aldrich, 20.8 ml of 1M solution in ethanol; 20.8 mmol) dropwise, over 15 minutes, at 20° C. Precipitate formation was observed before addition was complete. The flask was wrapped in foil and left to stir for 17 h. The reaction mixture was filtered in air, the solid washed on the filter frit with aqueous ethanol (60% ethanol v/v, 50 ml) and air-dried for 5 minutes to give 1.408 g of the target compound as a yellow solid (59% yield). Traces of ethanol and water were removed by heating the yellow solid under vacuum for 2 h at 50° C. ¹H nmr (in CDCl₃) showed the product to be an 80:20 mixture of trans:cis isomers.

EXAMPLE 2

Preparation of(ethylenebis-indenyl)zirconium (Me₂N-dpbd) (EBIZr(Me₂N-dpbd))

(Ethylenebis-indenyl)zirconium dichloride (Witco, 0.419 g, 1 mmol) and (Me₂N-dpbd) (as prepared in Example, 0.249 g, 1 mmol) were weighed into a flask in a glovebox (<1 ppm O₂/H₂O). Toluene (freshly distilled over Na, 28 ml) was added and the slurry stirred with a magnetic stir bar for 2 h. n-Butyl lithium (Aldrich, 1.25 ml of 1.6M solution in hexane, 2 mmol) was added over 1 minute at 20° C. The mixture was stirred for 9 h at 20° C. and filtered in the glovebox (25–50 μm frit). 5 ml of solvent was removed from the solution under vacuum. The solution was left in a freezer (−35° C.) for 36 h, and yellow crystals of unreacted diene removed by filtration. The solution was concentrated to approximately half volume under vacuum, and replaced in the freezer for 16 h to give a mixture of brown/black solid and yellow crystals, isolated by filtration and shown by $^1$H nmr to be a mixture of target product and unreacted diene (85:15 molar ratio).

EXAMPLE 3

Supported Catalyst Preparation

TEA-treated silica was prepared as follows:

20kg of Crosfield ES70 (activated at 500° C.) were slurried in 110 liters of hexane. 31.91 liters of 0.940M TEA in hexane were added (1.5 mmol Al/g silica), and the slurry agitated for 2 hours at 30° C. The silica was allowed to settle. and the supernateant hexane removed. The silica was further washed with hexane, until the concentration of Al in the washing had reached >1 mmol Al/liter. Then the silica was dried in vacuo at 60° C. A portion of the TEA-silica (1 g) was then slurried in hexane (Aldrich, dry, 5 ml) in a glovebox (<1 ppm $O_2/H_2O$). The solid prepared in example 2 (8.1 mg) was dissolved in hexane (Aldrich, dry, 5 ml) to give a very intense red/brown solution, added to the TEA/silica/hexane slurry and shaken. The settled solid was coloured red/brown, and the supernatent was completely colourless. A further sample of solid (3.0 mg) was dissolved in hexane (Aldrich, dry, 5 ml) and added to the slurry in the same way. The settled solid did not appear to change colour, but the supernatent was again completely colourless. The supernatent was decanted from the solid and used to dissolve tris(pentafluorophenyl)boron (Witco, 8.9 mg, 17.3 μmol), which was added to the treated silica with shaking. The solvent was removed under vacuum to give a pink free-flowing solid.

EXAMPLE 4

Supported Catalyst Preparation

A portion of the TEA-silica (1.094 g) prepared above was slurried in hexane (Aldrich, dry, 5 ml) in a glovebox (<1 ppm $O_2/H_2O$). The solid prepared in example 2 (40.5 mg) was dissolved in hexane (Aldrich, dry, 20 ml) to give a very intense red/brown solution. Aliquots of this solution (3 ml) were added to the TEA/silica slurry, which was shaken and allowed to settle. Addition was continued until the supernatant remained slightly coloured. About 10 ml of the supernatent was decanted from the solid and used to dissolve tris(pentafluorophenyl)boron (Witco, 25.3 mg, 49.4 μmol), which was added to the treated silica with shaking. After 30 minutes the solvent was removed under vacuum to give a pink free-flowing solid.

EXAMPLE 5

Preparation of (tert-butylamido) ($\eta^5$-tetramethylgyclopentadienyl)dimethylsilanetitanium ($Me_2$N-dpbd)

To a solution of 185 mg (0.502 mmol) dimethylsilyl (tetramethylcyclopentadienyl)(tert-butylamido)titanium dichloride and 125 mg (0.502 mmol)1-(4-dimethylaminophenyl)-4-phenyl-butadiene in 20 ml of toluene were added 0.628 ml n-BuLi (1.6 M in hexane) at 0° C. The dark purple mixture was stirred for 12 h at room temperature. The $^1$H-NMR showed only 50% conversion, so another 0.650 ml n-BuLi were added and the reaction stirred for another 12 h. 5 ml of hexane were added. Filtration of the solution after cooling to 20° C. and evaporation of the solvent from the filtrate led to isolation of a purple powder which contained 25% mol of free diene ($Me_2$N-dpbd) and 75% mol of the complex $(CH_3)_2Si(C_5(CH_3)_4)(NC(CH_3)_3)$Ti($Me_2$N-dpbd).

EXAMPLE 6

Supported Catalyst Preparation

Solid from example 5 (20.0 mg) was partially dissolved in hexane (Aldrich, dry, 15 ml) and the intensely-coloured red/brown solution added to TEA-treated silica (example 3, 1 g) slurried in hexane (Aldrich, dry, 10 ml) with shaking. The settled solid was red/brown and the supernatent completely colourless. The supernatent was decanted, and to the solid was added the residual solid which was dissolved in toluene (Aldrich, dry, 5 ml). The supernatent was completely decolourised after shaking and allowing the solid to settle. The slurry was filtered, washed and toluene (Aldrich, dry, 5 ml) on the frit and nitrogen-dried to give a pink/purple solid. Tris(pentafluorophenyl)boron (Witco, 19 mg, 37 μmol) was dissolved in hexane (Aldrich, dry, 10 ml) and the solid added to the solution with shaking. The solvent was removed under vacuum to give a pink/purple, free-flowing solid.

EXAMPLE 7

Ethylene/1-Hexene Copolymerisation Using Supported Catalysts

Tests were carried out in a 2.5 l stirred steel autoclave, which was first purged with nitrogen (95° C., 1.5 h). To the reactor was added dry sodium chloride (300 g) and potassium hydride (0.54 g) and heating continued (95° C., 1 h) before cooling to 73° C. Ethylene was added to obtain a pressure of 0.8 Mpa, and the required quantity of 1-hexene added via an HPLC pump. Catalyst was injected under nitrogen pressure into the stirred reactor and the temperature raised to 75° C. The reactor was maintained at 75° C. and ethylene and 1-hexene were supplied to maintain constant pressure and ethylene/1-hexene ratio over the duration of the reaction. The reactor was then cooled to 20° C. and the pressure vented. Polymer product was removed, washed with methanolic hydrogen chloride followed by aqueous ethanol, dried (in vacuo, 50° C.) and weighed to obtain a yield.

Results for supported catalysts prepared in examples 3, 4 and 6 are given in the Table.

| Example (Catalyst) | Quantity of catalyst injected/g | Quantity of 1-hexene injected/ml | Reaction time/min | Weight of polymer recovered/g | Activity g/g catalyst .h.b |
|---|---|---|---|---|---|
| 3 | 0.232 | 0.4 | 121 | 71.7 | 19 |
| 4 | 0.22 | 0.8 | 121 | 147.6 | 40.2 |
| 6 | 0.212 | 0.8 | 123 | 23.9 | 6.9 |

EXAMPLE 8

Supported Catalyst Preparation

TEA-treated silica (prepared according to example 3, 3 g) was slurried in toluene (dry, 15 ml). To this was added a toluene solution of tris(pentafluorophenyl)boron (Boulder Scientific, concentration 7.85% w/w; 45 μmol borane) followed by a toluene solution of complex EBIZr(Me$_2$N-dpbd) (example 2, 15 ml, 45 μmol Zr). The slurry was agitated then solvent removed under vacuum to leave a brick red, free-flowing solid.

EXAMPLE 9

Supported Catalyst Preparation

The method of example 8 was used, except the order of addition of tris(pentafluorophenyl)boron and EBIZr(Me$_2$N-dpbd) was reversed. A brick red, free-flowing solid was obtained.

EXAMPLE 10

Comparative Example—Supported Catalyst Preparation

The method of example 8 was used, except that a toluene solution of ethylenebis-indenyl)zirconium trans-(1,4-diphenylbutadiene) (Boulder Scientific, concentration 1.32% w/w) was used in place of the toluene solution of dimethylamino-functionalised analogue EBIZr(Me$_2$N-dpbd). A brick red, free-flowing solid was obtained.

EXAMPLES 11–15

Ethylene/1-Hexene Copolymerisation

Tests were carried out in a 2.5 l stirred steel autoclave, which was first purged with nitrogen (95° C., 1.5 h). To the reactor was added dry sodium chloride (300 g) and tri-isobutylaluminium-treated silica (TIBA-SiO$_2$, 0.6 g) prepared as follows: silica (Grace Davison 948, 50 g) was fluidised in a dry nitrogen flow. The temperature was raised to 200° C. over 2 h and held for 5 h before cooling to 100° C. over 1 h. To the fluidised silica was added a hexane solution of tri-isobutylaluminium (1M, 75 ml), and the fluidisation continued for a further 1 h, after which the treated silica was cooled to room temperature and transferred anaerobically to an inert atmosphere glove box. The reactor was set to 70° C. Ethylene was added to obtain a pressure of 0.65 Mpa, and the required quantity of 1-hexene added via a mass flow controller. Catalyst was injected under nitrogen pressure into the stirred reactor together with a further quantity of TIBA-SiO$_2$ (0.4 g). The reactor was maintained at 70° C. and ethylene and 1-hexene were supplied to maintain constant pressure and ethylene/1-hexene ratio over the duration of the reaction. The reactor was then cooled to 30° C. and the pressure vented. Polymer product was removed, washed with water and methanolic hydrogen chloride followed by aqueous ethanol, dried (in vacuo, 50° C.) and weighed to obtain a yield.

Results for supported catalysts prepared in examples 8–10 are given in the Table below.

EXAMPLE 16

Preparation of (tert-butylamido) (η$^5$-tetramethylcyclopentadienyl)dimethylsilanetitanium (Me$_2$N-dpbd)

(tert-butylamido)(η$^5$-tetramethylcyclopentadienyl) dimethylsilanetitanium dichloride (0.368 g, 1 mmol) and Me$_2$N-dpbd (according to example 1, 0.249 g, 1 mmol) were slurried in toluene (dry, 30 ml). n-Butyl lithium (Aldrich, 2 mmol, 1.25 ml of 1.6M hexane solution) was added at 40° C. and stirred for 16 h. The solution was filtered and solvent removed under vacuum. The solid was washed with hexane (Aldrich, dry, 15 ml), filtered and residual hexane removed under vacuum to leave a dark solid. $^1$H NMR analysis showed this to be a 1.4:1 molar ratio of the title compound and free starting diene.

EXAMPLE 17

Supported Catalyst Preparation

The solid of example 16 (72.5 mg) was dissolved in toluene (dry, 5 ml) and added to a toluene (dry, 20 ml) slurry of TEA-SiO$_2$ (according to example 2, 5 g) at 20° C. with shaking. On settling, the supernatant was clear and the solid darkly coloured. The solvent was removed under vacuum to give a purple free-flowing solid. This solid (2 g) was slurried in toluene (dry, 6 ml) and to it added a toluene solution (4 ml) of tris(pentafluorophenyl)boron (Boulder Scientific, 20.5 mg) with shaking. There was no obvious colour change or colouration of the supernatant. The solvent was removed under vacuum, leaving a dark purple free-flowing solid.

EXAMPLE 18

Ethylene/1-Hexene Copolymerisation

Polymerisation was carried out using the supported catalyst of example 17 according to the method described in example 7. The result is also given in the Table below.

| Example | Catalyst Example | Quantity of catalyst injected/ g | pC$_6^=$/pC$_2^=$ ratio of monomer partial pressures | Reaction time/ min | Weight of polymer recovered/ g | Activity g/g catalyst. h.b |
|---|---|---|---|---|---|---|
| 11 | 8 | 0.105 | 0.00687 | 90 | 79 | 75.7 |
| 12 | 8 | 0.11 | 0.00672 | 91 | 102 | 95 |
| 13 | 9 | 0.14 | 0.00674 | 91 | 95 | 68.3 |
| 14 | 10 | 0.103 | 0.00657 | 91 | 55 | 55.6 |
| 15 | 10 | 0.102 | 0.00649 | 91 | 54 | 50.9 |
| 18 | 17 | 0.205 | 0.8 | 122 | 40.9 | 11.4 |

We claim:

1. A transition metal complex suitable for use in the polymerization of olefins comprising a complex of formula:

L$_x$Q$_y$M-D wherein
 M is titanium, zirconium or hafnium in the +2 or +4 oxidation state,
 L is a group containing a cyclic delocalised anionic π system through which the group is bound to M,
 Q is a moiety bound to M via a σ-bond comprising boron or a member of Group 14 of the Periodic Table and also comprising nitrogen, phosphorus, sulphur or oxygen, said moiety having up to 60 non-hydrogen atoms,
 x=1 or 2
 y=0 or 1
 such that when x=1, y=1 and when x=2, y=0,
 D is a neutral, conjugated or non-conjugated unsaturated moiety optionally substituted with one or more hydrocarbyl groups, said D having up to 40 carbon atoms and forming a π complex with M when M is in the +2 oxidation state and a σ complex with M when M is in the +4 oxidation state and having at least one Lewis Base group B.

2. A complex according to claim 1 wherein M is titanium, y=1, x=1 and Q is represented by Z—Y wherein:
Y is —O—, —S—, NR*—, —PR*—, and
Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein:
R* each occurrence is independently hydrogen, or a member selected from hydrocarbyl, silyl, halogenated alkyl, halogenated aryl, and combinations thereof, said R* having up to 10 non-hydrogen atoms, and optionally, two R* group from Z when R* is not hydrogen, or an R* group from Z and R* group from Y form a ring system.

3. A complex according to claim 1 having the formula:

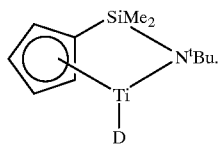

4. A complex according to claim 1 wherein M is zirconium, y=0 and x=2.

5. A complex according to claim 1 having the formula:

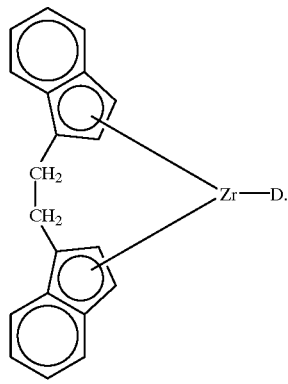

6. A transition metal complex suitable for use in the polymerisation of olefins comprising a complex having the formula:

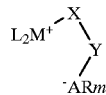

wherein
L is a group containing a cyclic delocalised anionic π system through which the group is bound to M,
M is a metal atom of group IIIB, IVB, VB or VIB of the Periodic Table
X is a heteroatom or hydrocarbyl group having 1–40 carbon atoms
Y is a hydrocarbyl group having 1–40 carbon atoms, and wherein X and/or Y contain at least one Lewis Base Group B, and
A is a metal atom of Group IB, IIB, IIIA, IIIB, IVA, VA, VB, VIB, VIIB or VIIIB of the Periodic Table
R are identical or different and are each a perhalogenated $C_1$–$C_{40}$ hydrocarbon radical, and m=1–5.

7. A complex according to claim 1 wherein the D group is a diene.

8. A complex according to claim 1 wherein the Lewis Base group B is chosen from

—$NR_2$, —$PR_2$, $AsR_2$, —OR, —SR wherein R may be hydrogen, halogen, $C_1$–$C_{20}$ aryl, $C_7$–$C_{40}$ alkylaryl, $C_7$–$C_{40}$ arylalkyl, $C_8$–$C_{40}$ arylalkenyl and may be the same or different or may be linked to form cyclic species containing between 2–20 carbon atoms.

9. A complex according to claim 1 wherein the D group is 1-phenyl-4($N,N^1$-dimethylaminophenyl) 1,3-butadiene.

10. The complex (ethylene bis-indenyl) zirconium (1-phenyl-4-(N,N'-dimethylaminophenyl)-1,3-butadiene.

11. The complex (tert-butylamido) ($n^5$-tetramethylcyclopentadienyl) dimethylsilanetitanium (1-phenyl-4-(N,N'-dimethylaminophenyl) 1,3-butadiene.

12. A supported catalyst system suitable for use in the polymerization of olefins comprising:
(A) transition metal complex of formula:

$L_xQ_yM$-D wherein
M is titanium, zirconium or hafnium in the +2 or +4 oxidation state,
L is a group containing a cyclic delocalised anionic π system through which the group is bound to M,
Q is a moiety bound to M and L via a σ-bond comprising boron or a member of Group 14 of the Periodic Table and also comprising nitrogen, phosphorus, sulphur or oxygen, said moiety having up to 60 non-hydrogen atoms,
x=1 or 2
y=0 or 1
such that when x=1, y=1 and when x=2, y=0,
D is a neutral, conjugated or non-conjugated unsaturated moiety optionally substituted with one or more hydrocarbyl groups, said D having up to 40 carbon atoms and forming a π complex with M when M is in the +2 oxidation state and a σ complex with M when M is in the +4 oxidation state and having at least one Lewis Base group B, and
(B) a support.

13. A supported catalyst system according to claim 12 wherein the support is silica.

14. A catalyst system suitable for use in the polymerization of olefins comprising:
(a) a supported catalyst according to claim 12, and
(b) an activator or activating technique.

15. A catalyst system according to claim 14 wherein the activator is tris(pentafluorophenyl)borane.

16. A catalyst system according to claim 14 wherein the activator is a trialkylammonium tetrakis(pentafluorophenyl) borate.

17. A catalyst system according to claim 14 wherein the molar ratio of complex to activator is in the range 1:10000 to 100:1.

18. A catalyst system according to claim 17 wherein the molar ratio of complex to activator is in the range 1:10 to 1:1.

19. A method for preparing a supported catalyst system comprising the steps of (a) adding an activator in a suitable solvent to a support, (b) adding a transition metal complex according to claim 1 to the solution obtained from step (a), and (c) removing the solvent.

20. A process for the polymerisation of ethylene or the copolymerisation of ethylene and alpha-olefins having 3–10 carbon atoms comprising carrying out the process in the presence of a catalyst system according to claim 14.

21. A process according to claim 20 carried out in the gas phase.

22. A complex according to claim 6 wherein the D group is a diene.

23. A complex according to claim 6 wherein the Lewis Base group B is chosen from $-NR_2, -PR_2, AsR_2, -OR, -SR$ wherein R may be hydrogen, halogen, $C_1$–$C_{20}$ aryl, $C_7$–$C_{40}$ alkylaryl, $C_7$–$C_{40}$ arylalkyl, $C_8$–$C_{40}$ arylalkenyl and may be the same or different or may be linked to form cyclic species containing between 2–20 carbon atoms.

24. A complex according to claim 6 wherein the D group is 1-phenyl-4(N,N$^1$-dimethylaminophenyl) 1,3-butadiene.

25. A method for preparing a supported catalyst system comprising the steps of (a) adding an activator in a suitable solvent to a support, (b) adding a transition metal complex according to claim 6 to the solution obtained from step (a), and (c) removing the solvent.

* * * * *